(12) United States Patent
Gammons et al.

(10) Patent No.: US 8,894,698 B2
(45) Date of Patent: Nov. 25, 2014

(54) THERMAL THERAPY BODY WRAPS

(75) Inventors: Scott Gammons, Loudon, TN (US);
Clifford E. Gammons, Loudon, TN (US)

(73) Assignee: Adroit Medical Systems, Inc., Loudon, TN (US)

( * ) Notice: Subject to any disclaimer, the term of this patent is extended or adjusted under 35 U.S.C. 154(b) by 595 days.

(21) Appl. No.: 13/303,390

(22) Filed: Nov. 23, 2011

(65) Prior Publication Data
US 2012/0130457 A1    May 24, 2012

Related U.S. Application Data

(60) Provisional application No. 61/416,523, filed on Nov. 23, 2010.

(51) Int. Cl.
*A61F 7/02* (2006.01)
*A61F 7/00* (2006.01)

(52) U.S. Cl.
CPC ........... *A61F 7/02* (2013.01); *A61F 2007/0003* (2013.01); *A61F 2007/0008* (2013.01); *A61F 2007/0009* (2013.01); *A61F 2007/0035* (2013.01); *A61F 2007/0039* (2013.01); *A61F 2007/0056* (2013.01); *A61F 2007/0019* (2013.01); *A61F 2007/0024* (2013.01); *A61F 2007/0045* (2013.01)
USPC ............................ 607/108; 607/104; 607/112

(58) Field of Classification Search
CPC .............. A61F 7/02; A61F 2007/0018; A61F 2007/0022–2007/0027; A61F 2007/0029; A61F 2007/003; A61F 2007/0032; A61F 2007/0034; A61F 2007/0054; A61F 2007/0056

USPC .......................................... 607/104, 108, 112
See application file for complete search history.

(56) References Cited

U.S. PATENT DOCUMENTS

| | | | |
|---|---|---|---|
| 4,149,541 A | 4/1979 | Gammons et al. | |
| 4,353,359 A * | 10/1982 | Milbauer | 601/166 |
| 4,706,672 A * | 11/1987 | Jones | 607/112 |
| 4,718,429 A * | 1/1988 | Smidt | 607/104 |
| 5,755,275 A | 5/1998 | Rose et al. | |
| 5,785,716 A * | 7/1998 | Bayron et al. | 607/108 |
| 5,865,841 A | 2/1999 | Kolen et al. | |
| 5,891,187 A * | 4/1999 | Winthrop et al. | 607/96 |
| 6,030,412 A * | 2/2000 | Klatz et al. | 607/104 |
| 6,113,626 A * | 9/2000 | Clifton et al. | 607/96 |
| 6,176,869 B1 | 1/2001 | Mason et al. | |
| 6,375,673 B1 * | 4/2002 | Clifton et al. | 607/104 |
| 6,500,200 B1 * | 12/2002 | Kushnir | 607/104 |
| 6,551,348 B1 | 4/2003 | Blalock et al. | |

(Continued)

*Primary Examiner* — Linda Dvorak
*Assistant Examiner* — Kaitlyn Smith
(74) *Attorney, Agent, or Firm* — Knox Patents; Thomas A. Kulaga (57) ABSTRACT

Thermal therapy pads for providing a temperature controlled therapy to a portion of a patient's body. The pad includes an inner surface and an outer surface that define a tortuous path for the fluid flow throughout the pad. The pad receives a temperature controlled fluid from a pumping unit via an inlet, and the fluid circulates throughout the pad before being returned to the cooling unit via an outlet. The pads are configured to conform to the shape of the portion of the body receiving the therapy. One such pad is a convertible vest that has one configuration that covers the upper torso and another configuration that covers the back and arms. Another such pad wraps around the wrist after being secured at the thumb. Another pad conforms to the face of the patient.

13 Claims, 9 Drawing Sheets

(56) References Cited

U.S. PATENT DOCUMENTS

| | | | |
|---|---|---|---|
| 6,565,699 B1 | 5/2003 | Szczesuil et al. | |
| 6,648,905 B2 * | 11/2003 | Record et al. | 607/104 |
| 6,669,715 B2 * | 12/2003 | Hoglund et al. | 607/104 |
| 6,685,731 B2 * | 2/2004 | Kushnir et al. | 607/104 |
| 6,962,600 B2 | 11/2005 | Lennox et al. | |
| 7,089,995 B2 * | 8/2006 | Koscheyev et al. | 165/46 |
| 7,640,764 B2 | 1/2010 | Gammons et al. | |
| 7,823,625 B2 * | 11/2010 | Gammons | 165/46 |
| 7,896,910 B2 * | 3/2011 | Schirrmacher et al. | 607/104 |
| 8,273,114 B2 * | 9/2012 | Wasowski | 607/104 |
| 8,434,163 B1 * | 5/2013 | Nudo | 2/102 |
| 8,585,746 B2 * | 11/2013 | Ilcheva et al. | 607/108 |
| 2002/0096311 A1 | 7/2002 | Kushnir et al. | |
| 2002/0107558 A1 * | 8/2002 | Clifton et al. | 607/104 |
| 2003/0069621 A1 * | 4/2003 | Kushnir | 607/104 |
| 2003/0229385 A1 | 12/2003 | Elkins | |
| 2005/0256556 A1 * | 11/2005 | Schirrmacher et al. | 607/104 |
| 2006/0247745 A1 * | 11/2006 | Thompson | 607/108 |
| 2007/0068651 A1 | 3/2007 | Gammons et al. | |
| 2007/0085340 A1 * | 4/2007 | Gammons | 285/308 |
| 2008/0103567 A1 * | 5/2008 | Augustine et al. | 607/108 |
| 2008/0234788 A1 * | 9/2008 | Wasowski | 607/104 |
| 2009/0005841 A1 * | 1/2009 | Schirrmacher et al. | 607/108 |
| 2009/0062892 A1 * | 3/2009 | Ilcheva et al. | 607/108 |
| 2009/0099631 A1 * | 4/2009 | Augustine et al. | 607/104 |
| 2009/0199571 A1 * | 8/2009 | Creech et al. | 62/3.2 |
| 2009/0264969 A1 * | 10/2009 | Gammons | 607/104 |
| 2010/0106229 A1 | 4/2010 | Gammons et al. | |
| 2011/0022137 A1 * | 1/2011 | Ennis-Thomas et al. | 607/108 |
| 2011/0098792 A1 * | 4/2011 | Lowe et al. | 607/104 |
| 2011/0152983 A1 * | 6/2011 | Schirrmacher et al. | 607/104 |

* cited by examiner

THERMAL THERAPY BODY WRAPS

CROSS-REFERENCE TO RELATED APPLICATIONS

This application claims the benefit of U.S. Provisional Application No. 61/416,523, filed Nov. 23, 2010.

STATEMENT REGARDING FEDERALLY SPONSORED RESEARCH OR DEVELOPMENT

Not Applicable

BACKGROUND

1. Field of Invention

This invention pertains to thermal pads for applying temperature controlled therapy to parts of a person's body. More particularly, this invention pertains to a plurality of thermal pads that are readily configured to fit about various body portions and are connectable to a temperature controlled liquid fluid pumping unit.

2. Description of the Related Art

It is advantageous to selectively apply a thermal treatment to patients. Hypothermic treatment is useful for emergency treatment of injured persons, particularly those who have experienced head trauma. Cooling the brain immediately after a trauma event often can protect the brain and/or prevent or reduce injury to the brain. But, not only the brain benefits from cooling treatment. A common first aid for sports injuries is to apply ice or cooling to the injured area.

Cooling treatment is also useful for providing comfort. Many menopausal women have found relief from hot flashes by using cooling treatment to quickly lower their body temperature during the onset of a hot flash.

Physicians have used various devices and techniques to cool the human body, including pharmacological cooling and various types of mechanically induced cooling. Mechanically induced cooling approaches generally fall into one of three categories: conductive, convective, or evaporative. While different implementations have been tried, many are limited by lack of practicality, difficulty of use, ineffectiveness, and/or excessive power consumption.

BRIEF SUMMARY

Thermal therapy pads for providing a temperature controlled fluid to a portion of a patient's body are provided. In various embodiments, the thermal therapy pads includes a head pad, a wrist pad, a leg pad, a limb pad worn on the foot, a limb pad worn on the elbow, and a convertible vest. The pads include an inner surface to be disposed adjacent the patient's body and an outer surface. The inner and outer surfaces define tortuous conduits or passages between an inlet and an outlet in which fluid flows throughout the pad. In one embodiment, the pad has an innermost layer that is a non-woven material, two middle layers that are waterproof and flexible, and an outermost layer that is a resilient foam. The four layers are joined together with the two middle layers joined together at selected spots to define the fluid channels.

The head pad is a thermal therapy pad for applying temperature controlled therapy to a patient's head. The surfaces bound a primary section having three pairs of flaps that enclose the posterior of the cranium, the scalp, the forehead, and the neck. The pad provides accessibility to part or all of the scalp, and to part or all of the neck, while providing controlled temperature therapy to the remainder of the head. The pad receives fluid from a pumping unit via an inlet, and the fluid circulates throughout the pad before being returned to the pumping unit via an outlet.

Other embodiments of the thermal therapy pads provide for cooling of the face and/or portions of the head. In one such embodiment, a face pad is substantially rectangular with openings for the eyes, nose, and throat. In another embodiment, a cap pad includes two joined portions, each having substantially a one-fourth prolate spheroid shape, that is, similar to one-fourth each of a football shape. The cap pad is positionable on substantially any portion of the head to provide cooling. In one embodiment, the cap pad includes openings for eyes, nose, and mouth, such that the cap pad provides controlled cooling to the face.

Another embodiment of the thermal therapy pad provides for temperature controlled therapy of the wrist of a patient. The wrist pad includes an elongated portion with an opening at one end. Inserting the thumb through the opening anchors the wrist pad during wrapping and greater stability of the pad is provided. The wrist pad is less likely to twist, turn, or otherwise shift on the wrist. Such an embodiment provides for more controlled thermal therapy of the wrist even when the wrist is moved during a medical procedure.

In another embodiment, temperature controlled therapy of the leg of a patient is provided. The leg pad includes two sections that enclose a portion of the leg. In yet another embodiment, temperature controlled therapy of a limb of a patient is provided. The limb pad is smaller than the leg pad and includes two sections that are used for an ankle, foot, arm, or elbow. In some embodiments, the limb pad includes fold lines that allow the pad to bend or fold without crimping the fluid flow inside the pad. Such an embodiment provides increased flexibility of the limb while continuing to provide controlled cooling of the body part.

Yet another embodiment of a thermal therapy pad is a convertible vest that has two configurations. One such configuration applies thermal therapy to the upper body of the patient, including the back and chest. The other configuration applies thermal therapy to the back and arms of the patient. The convertible vest includes fasteners that secure the pad in each of the configurations.

BRIEF DESCRIPTION OF THE SEVERAL VIEWS OF THE DRAWINGS

The above-mentioned features will become more clearly understood from the following detailed description read together with the drawings in which.

DETAILED DESCRIPTION

Thermal pads 100 providing temperature controlled therapy to a patient 102 are disclosed. As used herein, the A and B suffixes or the hash or apostrophe appended to a reference number indicate a particular embodiment. When the reference number is used without the suffix, the generic component is being referenced, for example the thermal pad 100 refers generically to the therapy device, whereas 100-A, 100-B, etc. refer to specific embodiments of the thermal pad 100.

Figure 1:
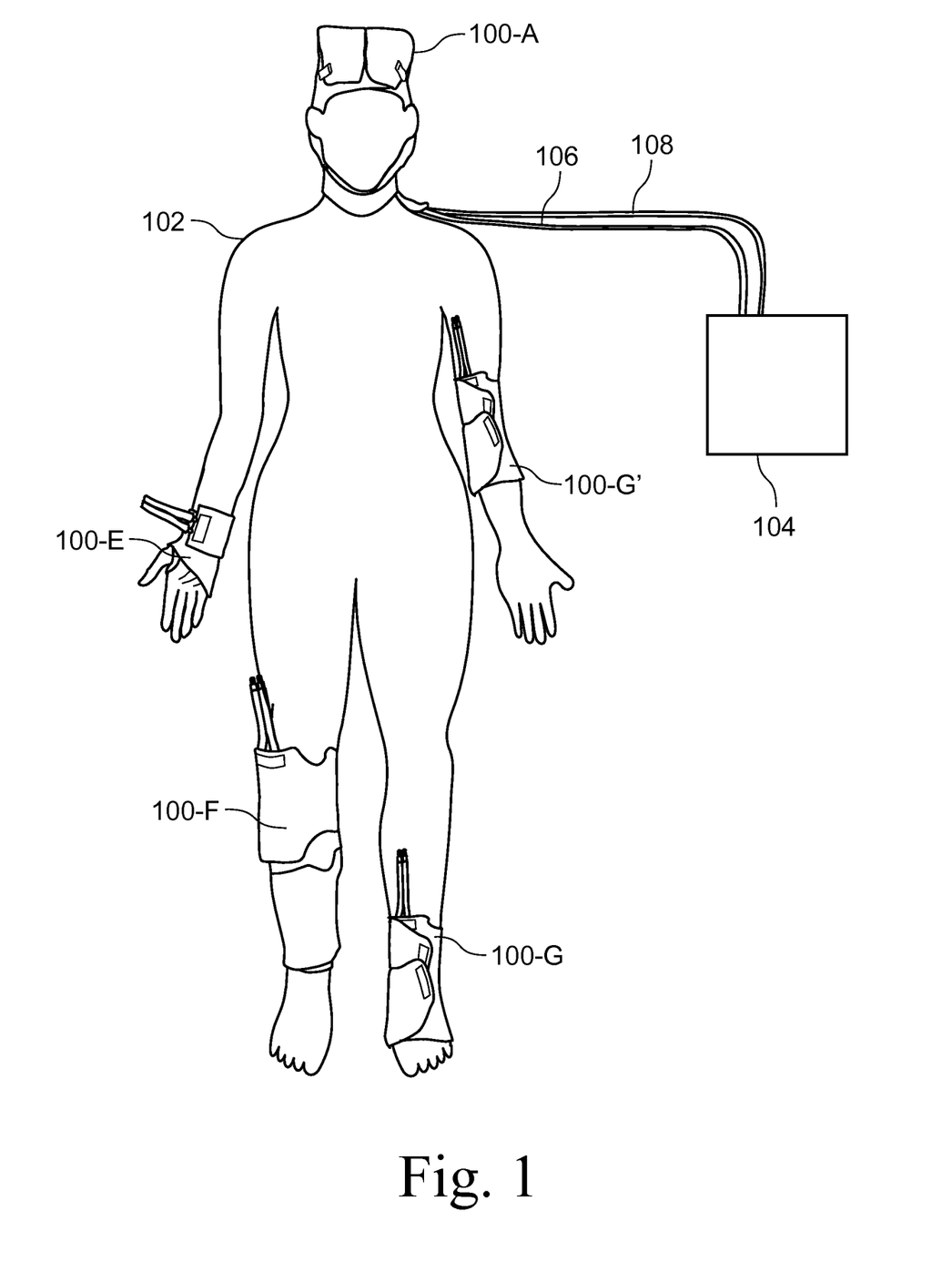
FIG. 1 is a front view of a patient and a portable cooling system with various embodiments of the thermal therapy pads.

FIG. 1 illustrates a front view of a patient 102 and a pumping unit 104 with the patient 102 wearing various embodiments of thermal pads 100. In various embodiments, a pumping unit 104 circulates thermally conditioned liquid, such as cooled water, through at least one thermal pad that is configured to enclose a particular body part or region of a patient 102 and to provide temperature controlled therapy to that body part. In the illustrated configuration, the patient 102 is outfitted with various embodiments of the thermal pads 100, including a head pad 100-A, a wrist pad 100-E, a leg pad 100-F, a limb pad 100-G worn on the foot, and a limb pad 100-G' worn on the elbow. The limb pad 100-G fits the foot, ankle, arm, or elbow. Other embodiments of the thermal pad 100 include a face pad 100-B, a cap pad 100-C, a neck pad 100-D, and a convertible vest 100-H.

Each thermal pad 100 includes an inlet tube 106 and an outlet tube 108 that are connectable to the pumping unit 104. The inlet and outlet tubes 106, 108 are in fluid communication with internal cooling channels of the thermal pad 100. The internal cooling channels vary according to the specific embodiment of the thermal cooling pad 100.

In the illustrated configuration, the head pad 100-A is connected to a pumping unit 104 via the inlet and outlet tubes 106, 108. In one embodiment, the pumping unit 104 is a portable cooling unit. The pumping unit 104 together with a thermal pad 100 provides a controlled rate of cooling or heating, as desired. The pumping unit 104 includes a fluid reservoir and a pump. The pump has an outlet in fluid communication with the inlet tube 106 of the pad 100. The outlet tube of the pad 100 is in fluid communication with the reservoir of the pumping unit 104. The inlet and outlet tubes 106, 108 are releasably connected to the pumping unit 104.

The pumping unit 104 pumps the liquid fluid through the connected head pad 100-A to provide cooling for the head and/or neck of the patient 102. In one embodiment, the pumping unit 104 uses cool water as the coolant. In one embodiment, the pumping unit 104 includes a switching unit for actuating the pumping unit 104 and a timer feature for shutting down the pumping unit 104 after a predetermined time. In another embodiment, the pumping unit 104 controls the water flow rate. In various configurations, one or more of the thermal pads 100 are connected to one or more pumping units 104.

Figure 2:
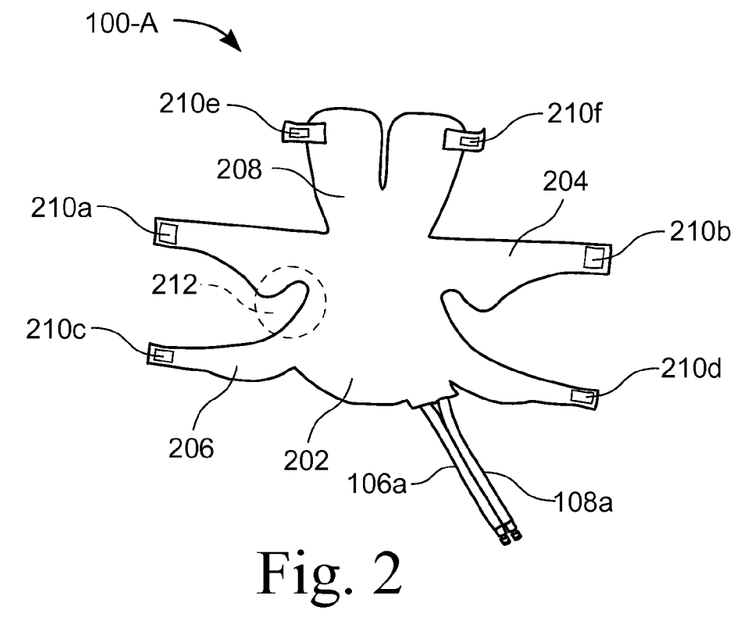
FIG. 2 is a plan view of one embodiment of a head pad in the open, flat position.
Figure 3:
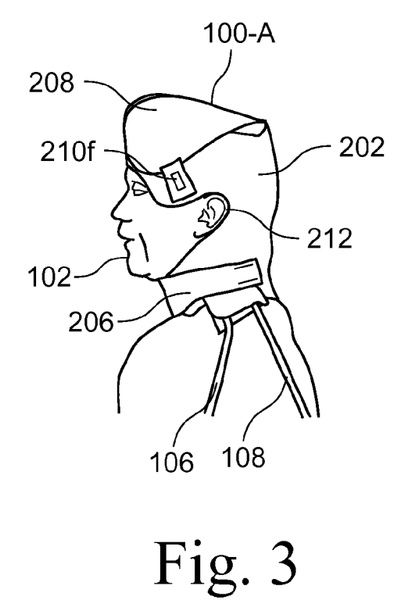
FIG. 3 is a side view of the head pad of FIG. 2 as worn by a patient.
Figure 4:
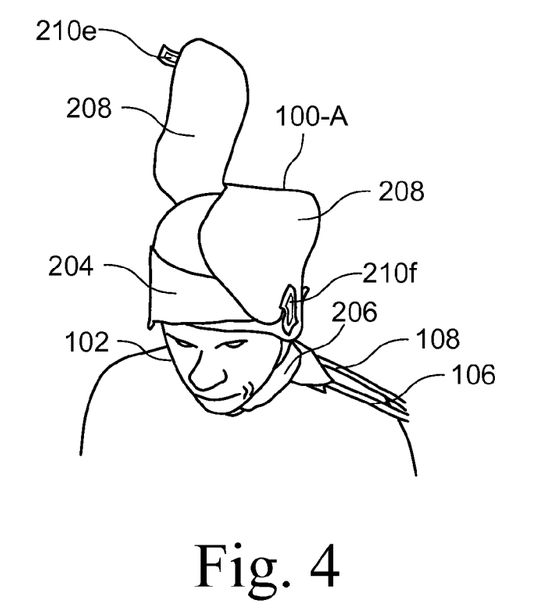
FIG. 4 is a perspective view of the head pad of FIG. 2 as worn by a patient.

FIG. 2 illustrates a plan view of one embodiment of a head pad 100-A in the open, flat position showing the outer surface. FIG. 3 illustrates a side view of the head pad 100-A as worn by a patient 102. FIG. 4 illustrates a perspective view of the head pad 100-A as worn by the patient 102. When connected to a cooling system, such as the pumping unit 104, the head pad 100-A provides for cooling the head and/or neck of the patient 102.

The illustrated embodiment of the head pad 100-A, is a flat pad with two surfaces. The head pad 100-A includes internal channels that form a tortuous conduit from the inlet tube 106a to the outlet tube 108a. The fluid flow is defined by the head pad 100-A. The head pad 100-A has a primary section 202, and includes first and second flaps 204, third and fourth flaps 206, fifth and sixth flaps 208, and inlet and outlet tubes 106a, 108a. The internal channels are included within the primary section 202, and the flaps 204, 206, 208.

The primary section 202 is dimensioned to enclose the posterior portion of a human skull when being worn by a patient 102. The first and second flaps 204, third and fourth flaps 206, and fifth and sixth flaps 208 extend from the primary section 202. The first and second flaps 204, third and fourth flaps 206, and fifth and sixth flaps 208 include fasteners 210a, 210b, 210c, 210d, 210e, 210f, respectively. When the flaps 204, 206, 208 are wrapped and fastened, the cranium and the neck of the patient 102 are enclosed. In one embodiment, the primary section 202 and the flaps 204, 206, 208 are made from a single unit that is composed of multiple layers of material as discussed in detail below.

The first and second flaps 204 extend laterally from the distal ends of respective edges between the proximal end and the distal end of the primary section 202 of the head pad 100-A. The distal end of the first and second flaps 204 includes a fastener 210a, 210b, such as the hook portion of a hook-and-loop fastener system. The fasteners 210a, 210b engage an exposed surface of the head pad 100-A, including other flaps, to secure the respective flap 204 to the head pad 100-A. The first and second flaps 204 each include a cut-out opening 212 between the respective flap 204 and the primary section 202 of the head pad 100-A. The cut-out opening 212 is an opening that accommodates a respective ear of the patient 102. The cut-out opening 212 also serves as a guide for properly situating the head pad 100-A on the head of the patient 102.

The third and fourth flaps 206 extend laterally from the proximal ends of the respective edges between the proximal end and the distal end of the primary section 202. The distal ends of the third and fourth flaps 206 also include a fastener 210c, 210d respectively. As above, the fastener 210 secures the respective flap 206 to the head pad 100-A.

The fifth and sixth flaps 208 extend distally from the anterior portion of the primary section 202. That is, the fifth and sixth flaps 208 are adjacent each other between the first and second flaps 204. In the open, flat position, the fifth and sixth flaps 208 extend from the primary section 202 in a substantially normal direction to the first and second flaps 204. The fifth and sixth flaps 208 each include fastener 210e, 210f near the distal end of the respective flap 204. The respective fasteners 210e, 210f of the fifth and sixth flaps 208 are oriented normal to the respective flaps 208 and opposite each other. That is, the fifth and sixth flaps 208 are adjacent each other and the respective fasteners 210e, 210f are located on the edge of the respective flap 208 that is opposite the other flap 208.

In the illustrated embodiment, the inlet and outlet tubes 106a, 108a extend from the proximal end of the primary section 202. In other embodiments, the inlet and outlet tubes 106a, 108a extend from the head pad 100-A at a convenient location that still provides for fluid flow within the head pad 100-A.

When worn by the patient 102, the head pad 100-A encloses the cranium and the neck. With each ear of the patient 102 positioned within a respective cut-out opening 212, the primary section 202 covers the rear of the cranium and the rear of the neck. The first and second flaps 204 each extend around and cover the forehead. Since both flaps 204 include a fastener 210a, 210b, the first and second flaps 204 are wrapped in either order so that the outermost flap 204 secures both flaps 204 in place.

The third and fourth flaps 206 each extend around and cover the portions of the neck not covered by the primary section 202. Since both flaps 206 include a fastener 210c, 210d, the second and third flaps 206 are wrapped in either order so that the outermost flap 206 secures both flaps 206 in place. Substantially, the entirety of the neck is enclosed by the second and third flaps 206 and the primary section 202.

The fifth and sixth flaps 208 extend from the primary section 202 to the forehead. The fifth and sixth flaps 208 cover the scalp of the patient 102. Each of the fifth and sixth flaps 208 is attached to either the first or the second flap 204 at the forehead.

The inlet and outlet tubes 106a, 108a are connected to a cooling system, such as a pumping unit 104. The pumping unit 104 pumps coolant, such as cool water, throughout the head pad 100-A and provides controlled cooling of the head of the patient 102.

The head pad 100-A provides access to portions of the head, such as the scalp or throat, while also providing controlled cooling of the head of a patient 102. Such access is particularly useful during surgery involving the throat or the scalp area. In a medical procedure involving the scalp, for example, the head pad 100-A continues to provide controlled cooling of the immediate area while providing access via simply opening one or both of the fifth and sixth flaps 208.

Limited throat access is provided without the necessity for opening the third and fourth flaps 206. More complete throat access is provided via opening one or both of the flaps 206.

The fifth and sixth flaps 208 provide access to the scalp area of the patient 102 while the remainder of the head pad 100-A continues to provide controlled cooling for the remainder of the head of the patient 102. Both the fifth and sixth flaps 208 are opened to provide complete access to the scalp portion of the cranium. If less access to the cranium is necessary, one flap 208 is opened while the other remains securely in position.

The third and fourth flaps 206 provide access to the neck area of the patient 102 while the remainder of the head pad 100-A continues to provide controlled cooling for the remainder of the head of the patient 102. Both the third and fourth flaps 206 are opened to provide complete access to the lateral and front portions of the neck. The remaining portions of the head pad 100-A continue to provide controlled cooling to the head of the patient 102.

Figure 5:
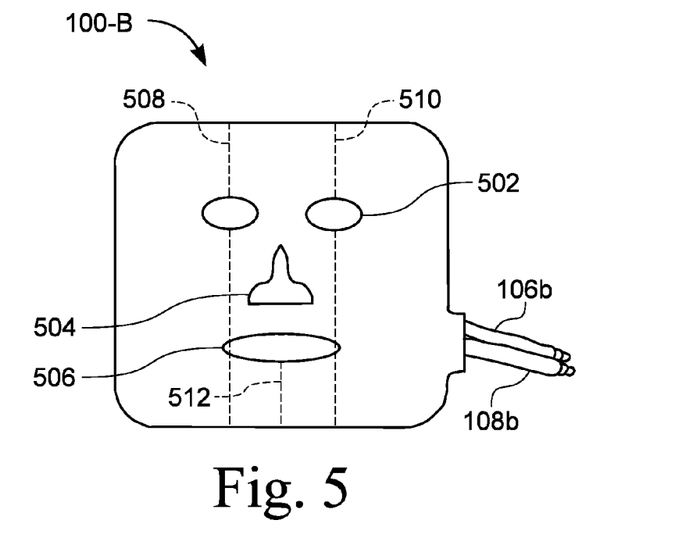
FIG. 5 is a plan view of one embodiment of a face pad.

FIG. 5 illustrates a plan view of one embodiment of a face pad 100-B. The face pad 100-B provides for thermal therapy of the face of the patient 102. In the illustrated embodiment, the face pad 100-B is a flat pad having a substantially rectangular shape, with two openings 502, a central opening 504, and a base opening 506. In one embodiment, the two openings 502 correspond to the eyes, the central opening 504 corresponds to the nose, and the base opening 506 corresponds to the mouth. In another embodiment, the face pad 100-B has a substantially oval shape, for example, to match the shape of a patient's face.

The face pad 100-B includes crease lines 508, 510, 512 to allow for access to a portion of the face while continuing to provide controlled cooling to the remainder of the face. The crease lines 508, 510, 512 allow the rectangular pad to follow the contour of the face of the patient 102. Crease lines 508, 510, 512 also allow the face pad 100-B to be folded away from either side of the face while the face pad 100-B continues providing cooling to the other side.

The crease lines 508, 510, 512 are configured to fold without disrupting the flow of liquid from the inlet tube 106b to the outlet tube 108b. When folded, the face pad 100-B does not crimp the internal fluid channels sufficiently to disrupt the flow of liquid throughout the pad 100-B.

When worn by the patient 102, the face pad 100-B provides controlled cooling for the face while medical procedures are performed on other parts of the body. In a folded position, the face pad 100-B also provides controlled cooling for a portion of the face while also allowing medical access to another portion of the face.

In the illustrated embodiment, the inlet and outlet tubes 106b, 108b extend from an edge of the face pad 100-B adjacent the base opening 506. In other embodiments, the inlet and outlet tubes 106b, 108b extend from the face pad 100-B at a convenient location that still provides for fluid flow within the face pad 100-B.

Figure 6:
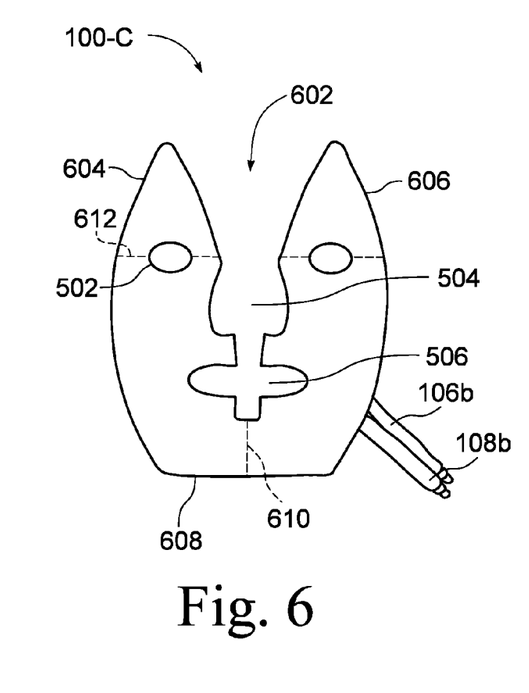
FIG. 6 is a plan view of one embodiment of a cap pad.
Figure 7:
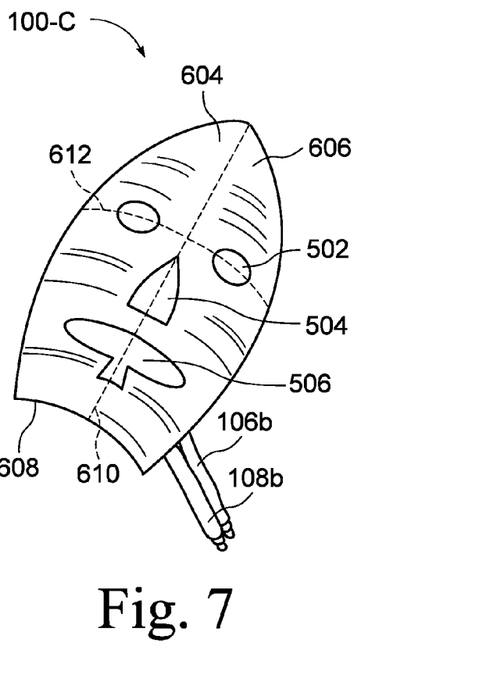
FIG. 7 is a perspective view of the cap pad of FIG. 6 partially folded as in use.

FIG. 6 illustrates a plan view of one embodiment of a cap pad 100-C. FIG. 7 illustrates a perspective view of the cap pad 100-C partially folded as when in use with the two portions 604, 606 joined at the crease line 610. In the illustrated embodiment, the cap pad 100-C is a face version that includes a section with a bifurcated opening 602. The bifurcated opening divides the section into two portions 604, 606. Each portion 604, 606 includes an elliptical opening 502. The bifurcated opening 602 also includes a central opening 504 and a base 506 opening. In one embodiment, the elliptical openings 502 correspond to the eyes, the central opening 504 corresponds to the nose, and the base opening 506 corresponds to the mouth.

Each portion 604, 606 extends along the polar axis of a shape that resembles a prolate spheroid. A prolate spheroid is substantially a football shape and is often defined in fourths extending lengthwise. Thus, the cap pad 100-C is shaped similar to two-fourths of a football. In the illustrated embodiment, a portion of the cap pad 100-C is truncated at a base 608. In another embodiment, the base 608 extends so that the cap pad 100-C is substantially one-half, or two-fourths, prolate spheroidal in shape.

The cap pad 100-C includes crease lines 610, 612 to allow for access to a portion of the face while continuing to provide controlled cooling to the remainder of the face. The crease lines 610, 612 allow the cap pad 100-C to be folded away from a portion of the face of the patient 102. Crease line 610 allows the cap pad 100-C to be folded away from one side of the face while the cap pad 100-C continues providing cooling to the other side. Similarly, crease line 612 allows the cap pad 100-C to be folded away from either the upper half or the lower half of the face, while the cap pad 100-C continues providing cooling to the other half of the face.

As with the face pad 100-B, the crease lines 610, 612 of the cap pad 100-C are configured to fold without disrupting the flow of liquid from the inlet tube 106b to the outlet tube 108b.

The cap pad 100-C does not crimp the internal fluid channels sufficiently to disrupt the flow of liquid throughout the pad 100.

When worn by the patient 102, the bifurcated sections 604, 606 are joined together so that the cap pad 100-C closely resembles a cap. In one such embodiment, the sections 604, 606 are joined permanently, such as by welding or heat-sealing or with an adhesive or tape. In another embodiment, a releasable fastener, such as a hook portion of a hook-and-loop fastening system joins the two 604, 606. Such a configuration provides controlled cooling for substantially the entire face of the patient 102. Because of the cap-like shape, the cap pad 100-C fits substantially any portion of the head of the patient 102 that requires controlled cooling. In one embodiment, the bifurcated opening 602 does not include openings for the eyes, nose, and mouth. In such an embodiment, the bifurcated opening 602 provides for closure of the space between the two sections and for controlled cooling without the additional openings of the face version that is illustrated in FIG. 6 and FIG. 7.

The cap pad 100-C provides for access to any part of the head that is not covered by the cap pad 100-C while also providing for controlled cooling in the area of the head that is covered. In a folded position, the cap pad 100-C also provides controlled cooling for a portion of the face or head while also allowing medical access to the uncovered portions of the face or head of the patient 102.

In the illustrated embodiment, the inlet and outlet tubes 106b, 108b extend from an edge of the cap pad 100-C adjacent the base opening 506. In other embodiments, the inlet and outlet tubes 106b, 108b extend from the cap pad 100-C at a convenient location that still provides for fluid flow within the cap pad 100-C.

Figure 8:
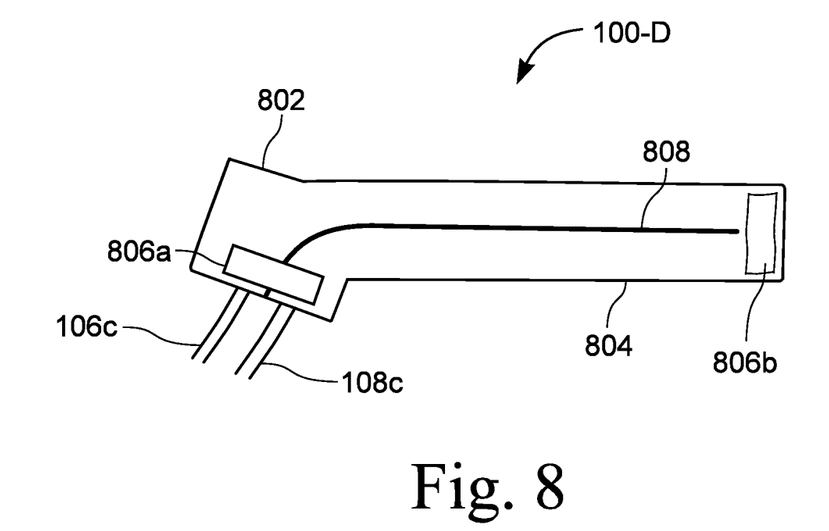
FIG. 8 is a plan view of one embodiment of a neck pad.
Figure 9:
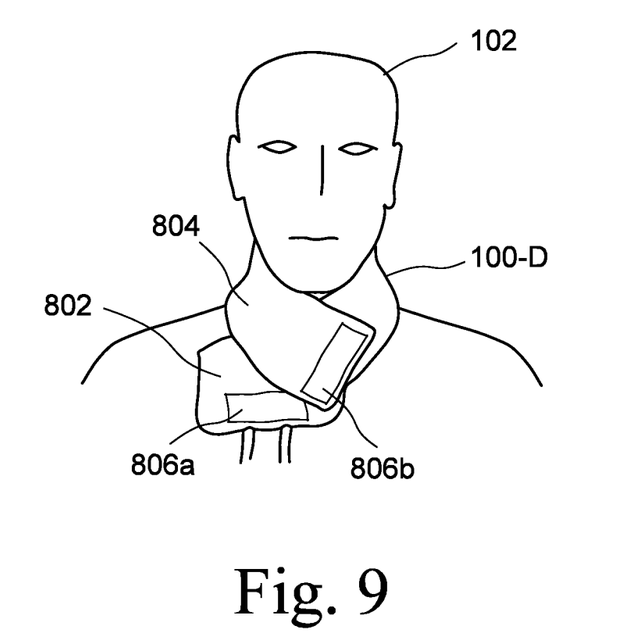
FIG. 9 is a front view of the neck pad of FIG. 8 as worn by a patient.

FIG. 8 illustrates a view of one embodiment of a neck pad 100-D. FIG. 9 illustrates a frontal view of the neck pad 100-D as worn by the patient 102. The neck pad 100-D includes a base section 802 and an elongated section 804. In the illustrated embodiment, the elongated section 804 extends from the base section 802 at an angle such that the base section 802 is not tilted or twisted as the elongated section 804 wraps around the neck of the patient 102.

In the illustrated embodiment, the base section 802 includes a fastener 806a proximate the inlet and outlet tubes 106c, 108c. The elongated section 804 also includes a fastener 806b distal to the base section 802. In the illustrated embodiment, the fastener 806b is illustrated on the outer surface of the neck pad 100-D. In another embodiment, the fastener is secured to the inner surface of the pad 100-D. The elongated section 804 is of sufficient length to wrap around the neck of the patient 102 and secure the pad 100-D to itself. The fasteners 806a, 806b, in one embodiment, are the hook portion of a hook-and-loop fastener system. The surface of the pad 100-D has a surface to which the fastener 806a, 806b engages. The multiple locations of the fasteners 806a, 806b allows for flexibility in securing the pad 100-D around the neck.

In the illustrated embodiment, the inlet and outlet tubes 106c, 108c extend from the base section 802 of the neck pad 100-D. In other embodiments, the inlet and outlet tubes 106c, 108c extend from the neck pad 100-D at a convenient location that still provides for fluid flow within the neck pad 100-D. The neck pad 100-D includes a divider 808 that defines a channel that directs the fluid flow from the inlet 106c, through the pad 100-D, and to the outlet 108c.

When worn by the patient 102 as shown in FIG. 9, the elongated section 804 wraps around the neck such that the base section 802 rests against the upper portion of the chest or thorax of the patient 102. The neck pad 100-D provides controlled cooling to the neck of the patient 102 and also to the portion of the chest adjacent the base section 802 without hindering access to the surrounding portions of the body of the patient 102.

Figures 10, 11, 12:
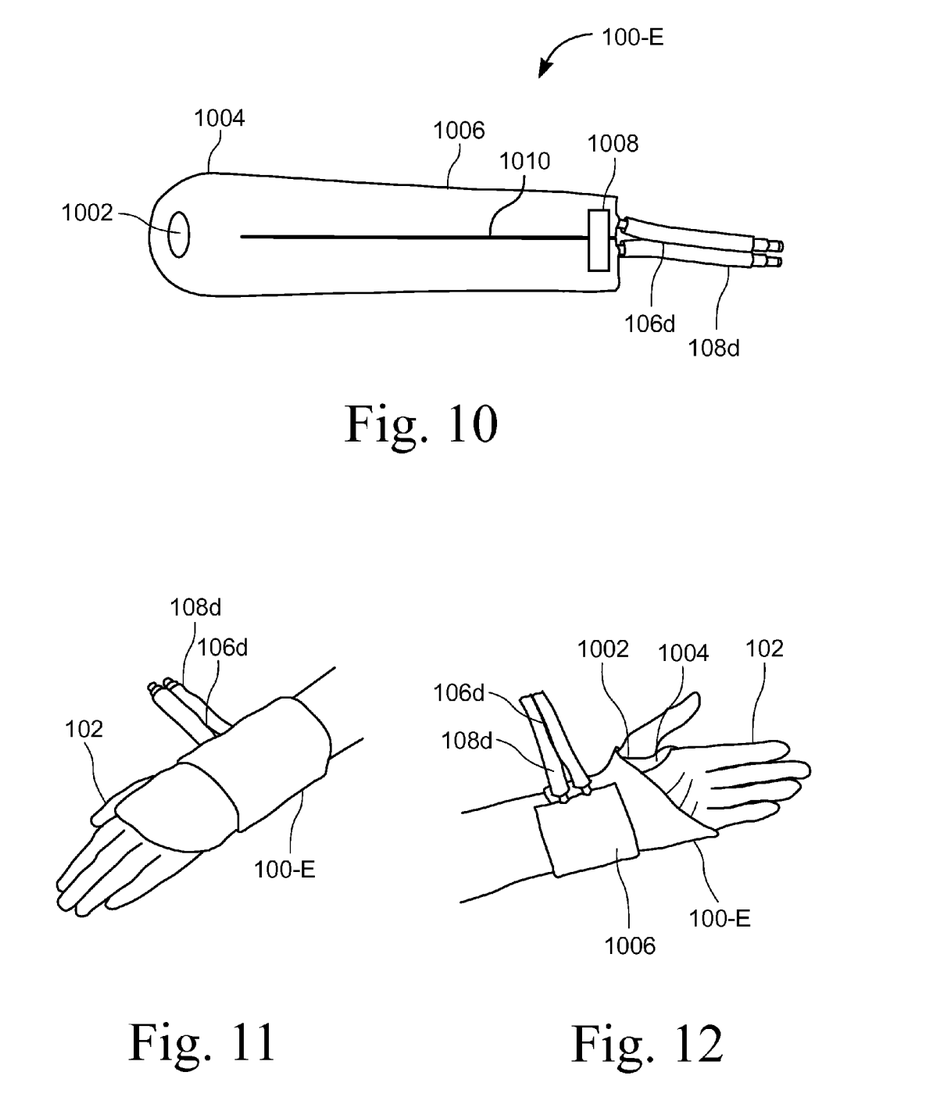
FIG. 10 is a plan view of one embodiment of a wrist pad.
FIG. 11 is a backhand perspective view of the wrist pad of FIG. 10 as worn by a patient.
FIG. 12 is a palm perspective view of the wrist pad of FIG. 10 as worn by a patient.

FIG. 10 illustrates a plan view of one embodiment of a wrist pad 100-E. FIG. 11 illustrates a backhand perspective view of the wrist pad 100-E as worn by the patient 102. FIG. 12 illustrates a palm perspective view of the wrist pad 100-E as worn by the patient 102. The wrist pad 100-E includes an oval opening 1002, a first section 1004, and a second section 1006. In one embodiment, the opening 1002 accommodates the thumb of the patient 102. That is, the patient's thumb fits through the oval opening 1002 of the wrist pad 100-E.

The wrist pad 100-E is of sufficient length that it can be wrapped at least once around the wrist area of a patient 102. In one embodiment, the wrist pad 100-E is of such length that when the patient's thumb is inserted through the opening 1002, the second section 1006 encloses the wrist with at least one complete turn encircling the wrist and arm, and is secured to itself via the fastener 1008. In one such embodiment, the wrist wrap encircles the wrist and arm twice and is secured to itself via the fastener 1008. In such an embodiment, the fastener 1008 is the hook portion of a hook-and-loop fastener system and the surface of the pad 100-E engages the hook portion of the fastener 1008.

In one embodiment, the first section 1004 together with the opening 1002 secures the wrist pad 100-E to the thumb of the patient 102. In this way, the wrist pad 100-E is anchored to the thumb during the wrapping around the wrist. Anchoring the wrist pad 100-E prior to wrapping provides for one handed application. Such an embodiment provides the capability for the patient to secure the wrist pad 100-E without assistance. Anchoring the wrist pad 100-E to the thumb also provides greater stability for the pad 100-E. In such an embodiment, the wrist pad 100-E does not twist, turn, or otherwise shift on the wrist of the patient 102.

In another embodiment, the first section 1004 includes two flaps that are joined with a fastener 210, such as a hook and loop fastener. In such an embodiment, the flaps are wrapped around the patient's thumb to secure the wrist pad 100-E to the thumb prior to wrapping. Such a configuration is useful where the thumb is partially enclosed by a splint or other apparatus that is braced to the wrist or arm such that the thumb cannot be inserted through an opening that is not fastenable.

When worn by the patient 102, the wrist pad provides controlled cooling for the wrist and/or hand of a patient 102. For example, in a medical procedure involving the hand or fingers, localized cooling is provided in a manner that allows the cooling to stay with the hand even when the hand must be moved or repositioned.

In the illustrated embodiment, the inlet and outlet tubes 106d, 108d extend from the end of the wrist pad 100-E distal to the opening 1002. In other embodiments, the inlet and outlet tubes 106d, 108d extend from the wrist pad 100-E at a convenient location that still provides for fluid flow within the wrist pad 100-E. In the illustrated embodiment, a divider 1010 extends from between the inlet and outlet tubes 106d, 108d toward the opening 1002. The divider 1010 directs the flow from the inlet tube 106d up one side of the pad 100-E and down the opposite side to the outlet tube 108d. In this way the thermally conditioned fluid is distributed over the surface of the pad 100-E with a minimal temperature gradient.

Figure 13:
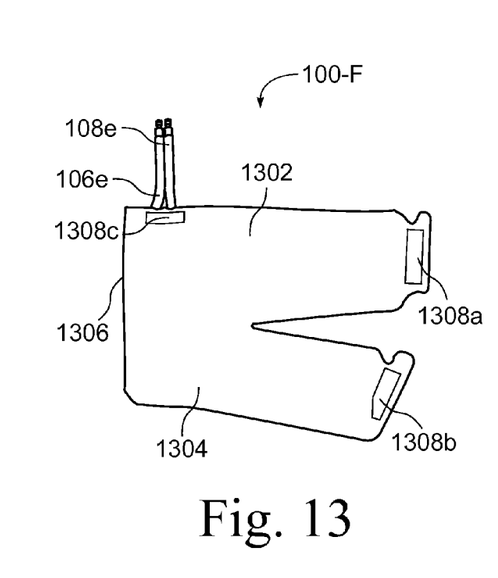
FIG. 13 is a plan view of one embodiment of a leg pad.
Figure 14:
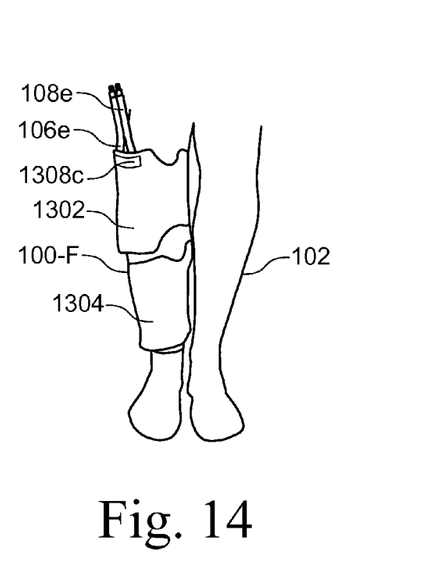
FIG. 14 is a front view of the leg pad of FIG. 13 as worn by a patient.

FIG. 13 illustrates a plan view of one embodiment of a leg pad 100-F. FIG. 14 illustrates a front view of the leg pad 100-F as worn by the patient 102. The leg pad 100-F includes a first portion 1302 and a second portion 1304. The first portion 1302 and the second portion 1304 are joined for a portion of their length at one end 1306 of the leg pad 100-F. The first portion 1302 and the second portion 1304 each include a fastener 1308a, 1308b at the respective end of the portion 1302, 1304 distal to the joined end of the leg pad 100-F. A fastener 1308c is also included proximate the inlet and outlet tubes 106e, 108e. In one embodiment, each of the fasteners 1308a, 1308b, 1308c is a hook portion of a hook-and-loop fastener system and the surface of the pad 100-F engages the hook portion of the fastener fasteners 1308a, 1308b, 1308c. The fasteners 1308a, 1308b, 1308c are positioned to aid securing the pad 100-F around the body.

The leg pad 100-F is of sufficient size and length for the first and second portions 1302, 1304 to wrap around a section of a leg of the patient 102. In the illustrated embodiment, the first portion 1302 is of greater length than the second portion 1304.

When worn by the patient 102, the first and second portions 1302, 1304 are each wrapped around the leg such that a fastener 210 secures the respective portion 1302, 1304 to itself. In one embodiment as illustrated in FIG. 14, the first portion 1302 is wrapped around the larger part of the leg of the patient 102. Since the first portion 1302 and the second portion 130 are separated, they each wrap separately around the leg of the patient 102. Wrapping the sections 1302, 1304 separately provides for flexure of the leg. Controlled cooling for the leg is provided while also maintaining leg mobility for the patient 102.

During medical procedures involving the foot, localized cooling is provided in a manner that allows the cooling to stay with the leg even when the foot must be moved or repositioned. Similarly, for medical procedures involving the hip or groin area, the leg pad 100-F is wrapped around the upper thigh to provide controlled cooling near the procedure area.

In the illustrated embodiment, the inlet and outlet tubes 106e, 108e extend from an edge of the first portion 1302 near the end of the leg pad 100-F distal to the fastener 210. In other embodiments, the inlet and outlet tubes 106e, 108e extend from the leg pad 100-F at a convenient location that still provides for fluid flow within the leg pad 100-F.

Figure 15:
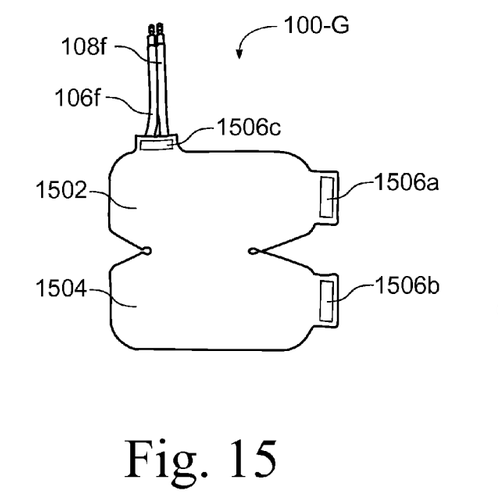
FIG. 15 is a plan view of one embodiment of a limb pad.
Figure 16:
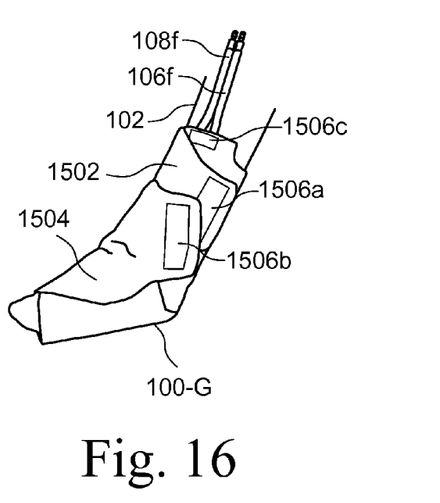
FIG. 16 is a perspective view of the limb pad of FIG. 15 as worn on the ankle and foot of a patient.

FIG. 15 illustrates a plan view of one embodiment of a limb pad 100-G. FIG. 16 illustrates a perspective view of the limb pad 100-G as worn on the ankle and foot of a patient 102. The limb pad 100-G includes a first portion 1502 and a second portion 1504. In the illustrated embodiment, the first portion 1502 and the second portion 1504 are equal in length and are joined for a portion of their length between the ends of the limb pad 100-G. The first portion 1502 and the second portion 1504 each include a fastener 1506a, 1506b at one end of the limb pad 100-G. A fastener 1506c is also included proximate the inlet and outlet tubes 106f, 108f. In one embodiment, each of the fasteners 1506a, 1506b, 1506c is a hook portion of a hook-and-loop fastener system and the surface of the pad 100-G engages the hook portion of the fastener fasteners 1506a, 1506b, 1506c. The fasteners 1506a, 1506b, 1506c are positioned to aid securing the pad 100-G around the limb.

The limb pad 100-G is of sufficient size and length for the first and second portions 1502, 1504 to wrap around a section of a foot, ankle, elbow, or arm of the patient 102. In the illustrated embodiment, the limb pad 100-G is wrapped around the ankle and foot of a patient 102.

When worn by a patient 102, the first and second portions 1502, 1504 are wrapped about the limb such that one of the portions 1502, 1504 is secured to itself by a fastener 210. The remaining portion 1502, 1504 is secured so that both portions 1502, 1504 are secured. In one configuration, the remaining portion 1502, 1504 is secured to both itself and the previously secured portion 1502, 1504.

In some embodiments, the limb pad 100-G includes crease lines that provide for folding the limb pad 100-G at the joints of the limb, such as the elbow or ankle, without disrupting the flow of liquid from the inlet tube 106f to the outlet tube 108f. In such embodiments, the limb pad 100-G does not crimp the internal fluid channels sufficiently to disrupt the flow of liquid throughout the limb pad 100-G.

In the illustrated embodiment, the inlet and outlet tubes 106f, 108f extend from an edge of the first portion 1502 near the end of the limb pad 100-G distal to the fastener 210. In other embodiments, the inlet and outlet tubes 106f, 108f extend from the limb pad 100-G at a convenient location that still provides for fluid flow within the limb pad 100-G.

Figure 17:
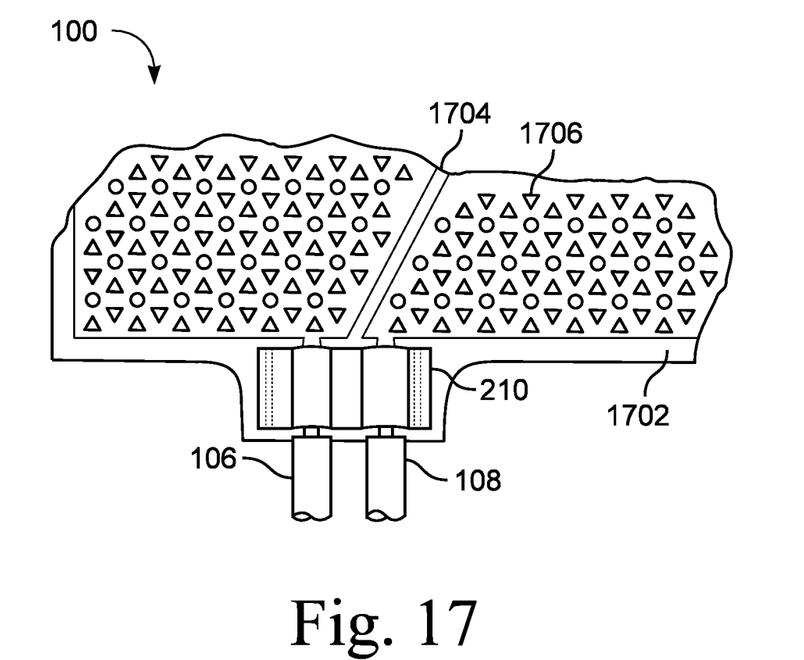
FIG. 17 is a partial view of one embodiment of a thermal therapy pad.
Figure 18:
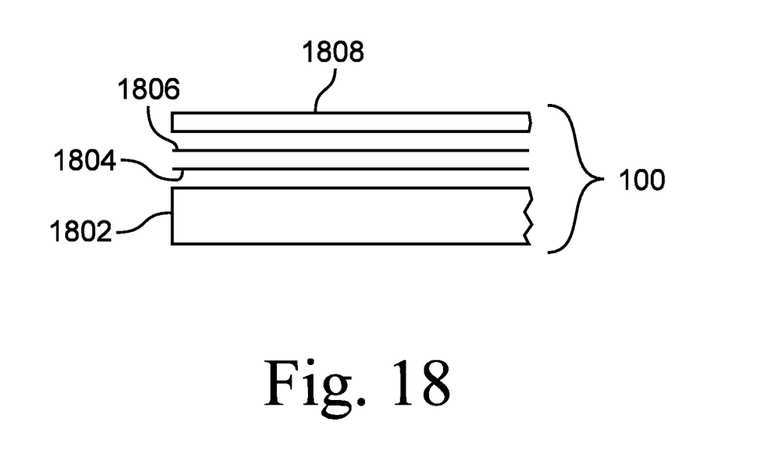
FIG. 18 is a partial exploded end view of one embodiment of a thermal therapy pad.

FIG. 17 illustrates a partial view of one embodiment of a thermal therapy pad 100. FIG. 18 is a partial exploded end view of one embodiment of a thermal therapy pad 100. The pad 100, in the illustrated embodiment, is made of four layers. The outermost layer 1802 is a layer approximately 3 mm thick. The outermost layer 1802 has a resilient foam on the inner side with a woven backing that is exposed on the outside surface. The middle layers 1804, 1806 are a material, such as plastic, that is waterproof and flexible. The middle layers 1804, 1806 are approximately 0.1 mm thick. The innermost layer 1808 is a non-woven material that may come in contact with the patient 102. To form the pad 100 the four layers 1802, 1804, 1806, 1808 are heat sealed or welded together at a border 1702, a dividing barrier 1704, and at selected spots 1706 to define fluid channels. The inlet and outlet tubes 106, 108 have plastic conduits that are positioned between the middle layers 1804, 1806 such that, when the layers 1802, 1804, 1806, 1808 are joined together, the inlet and outlet tubes 106, 108 are in fluid communication with the fluid channels formed between the middle layers 1804, 1806.

The layers 1802, 1804, 1806, 1808 are configured to allow the pad 100 to fold at the crease lines 508, 510, 606, 608 or to wrap without disrupting the flow of fluid from the inlet tube 106 to the outlet tube 108. That is, the pad 100 does not crimp the fluid channels sufficiently to disrupt the fluid flow when the pad 100 is folded or wrapped into its deployed configuration. The illustrated pad 100 includes a fastener 210, such as the hook portion of a hook-and-loop fastener system. The fastener 210 engages the exposed surface of either the outermost or the innermost layer 1802, 1808 to secure a selected portion of the pad 100. For example, the fastener 210 engages a portion of the pad 100 that is proximate the fastener 210 when the pad 100 is folded at a crease line 508, 510, 606, 608 or otherwise draped to conform to the shape of the body portion being treated. In this way the pad 100 retains its shape when the pad 100 is formed into a particular shape and the pad 100 is secured to the patient 102.

Figure 19:
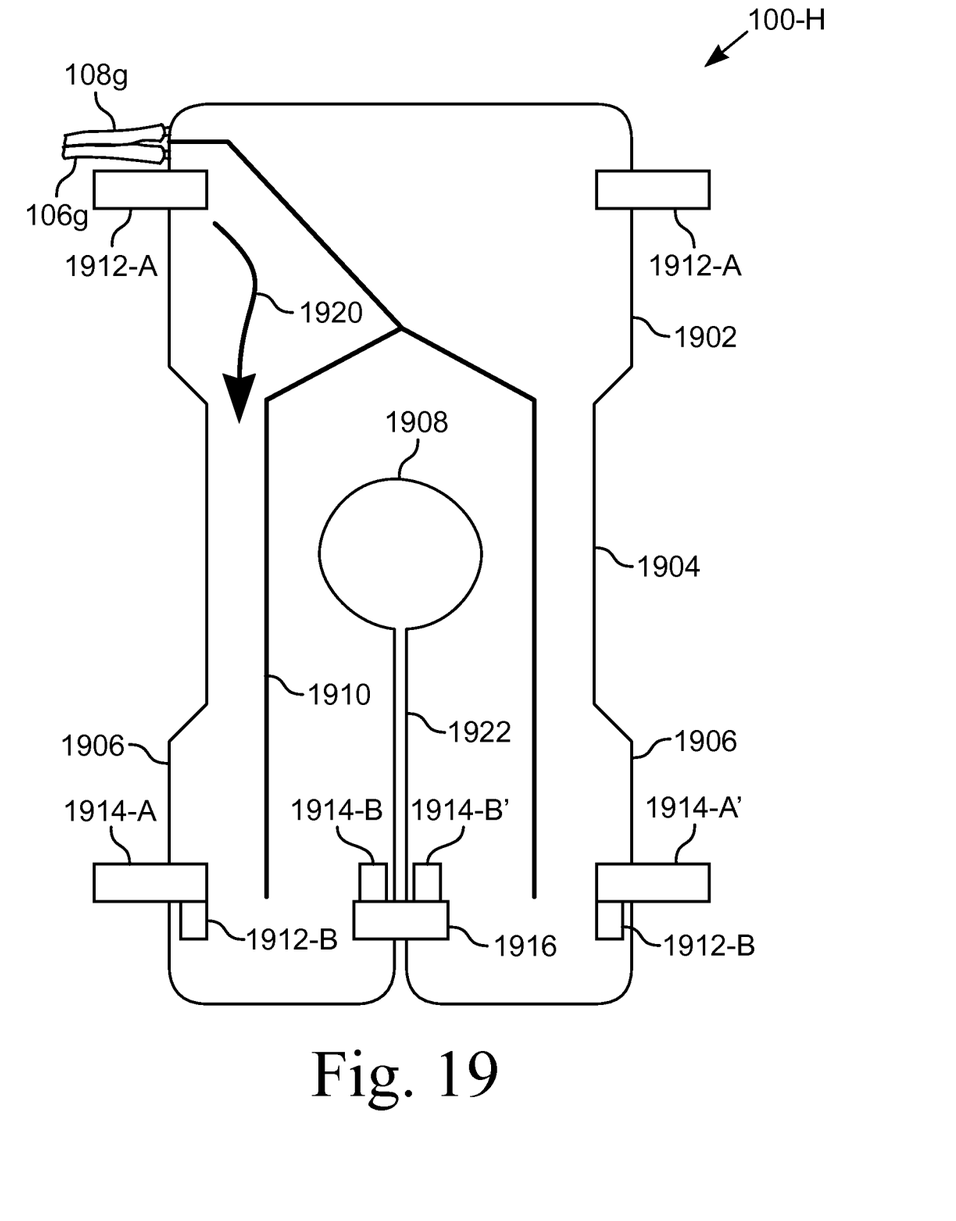
FIG. 19 is a plan view of one embodiment of a convertible vest pad.
Figure 20:
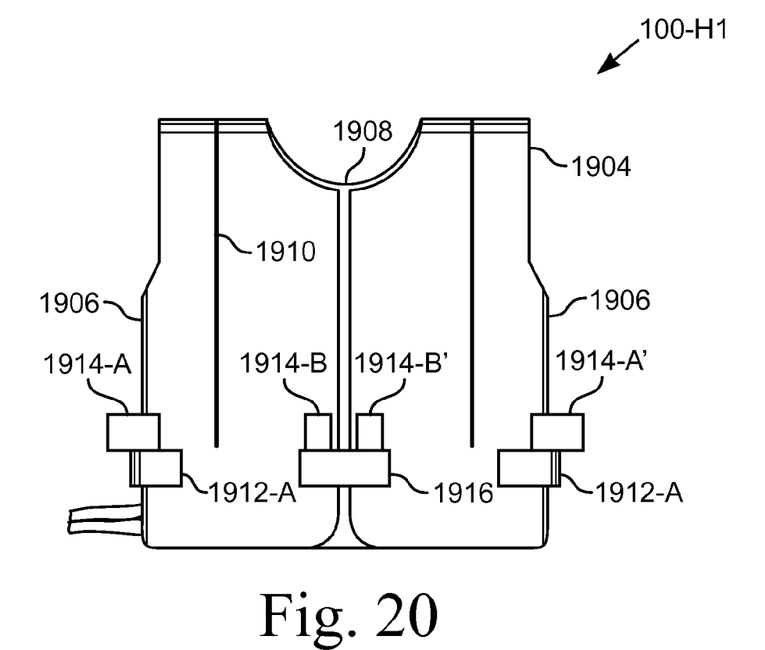
FIG. 20 is a front view of one embodiment of a convertible vest pad in a vest configuration.
Figure 21:
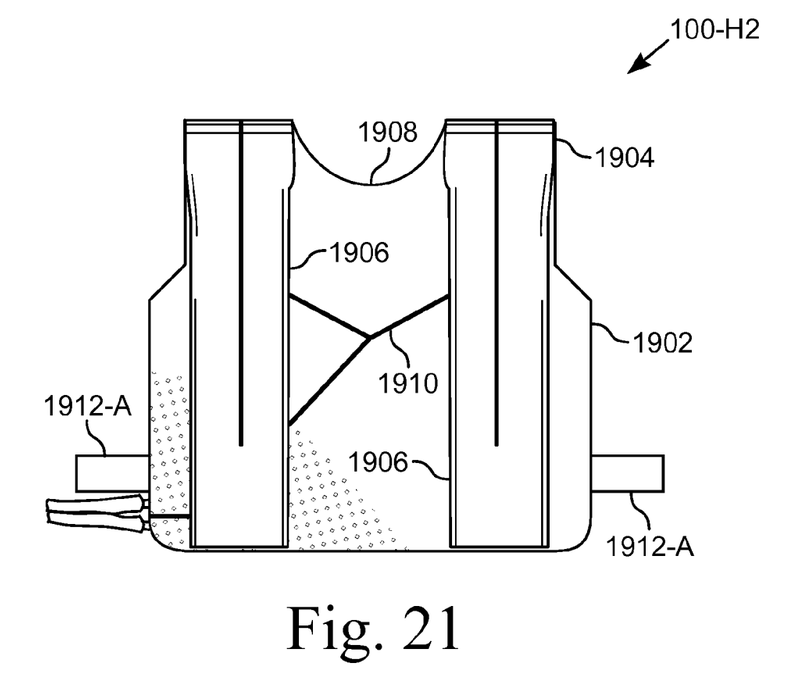
FIG. 21 is a front view of one embodiment of a convertible vest pad in an arm-covering configuration.

FIG. 19 illustrates a plan view of one embodiment of a convertible vest pad 100-H. The thermal pad 100-H is a planar pad that has a back portion 1902, a shoulder portion 1904 with a neck opening 1908, and a front portion 1906 that is in two pieces. FIG. 20 illustrates a front view of one embodiment of a convertible vest pad 100-H in a vest configuration, or first deployed configuration, 100-H1. FIG. 21 illustrates a front view of one embodiment of a convertible vest pad 100-H in an arm-covering configuration, or second deployed configuration, 100-H2. The thermal pad 100-H is a convertible vest that has a first deployed configuration 100-H1 that is a vest, which is illustrated in FIG. 20, and a second deployed configuration 100-H2 that is a back and arm pad, which is illustrated in FIG. 21.

The back portion 1902 and the front portion 1906 are wider than the shoulder portion 1904 to allow the sides of the back and front portions 1902, 1906 to wrap around the patient 102 and join together when the convertible vest pad 100-H is fitted to a person 102. The convertible vest pad 100-H is sized such that the back portion 1902 substantially covers the back of the patient 102 when the shoulder portion 1904 is positioned over the shoulders of the patient 102. The front portion 1906 of the convertible vest pad 100-H is sized such that each half of the front portion 1906 is long enough to wrap around an arm of the patient 102.

The back portion 1902 includes an inlet tube 106d and an outlet tube 108d. The inlet and outlet tubes 106g, 108g are in fluid communication with internal cooling channels of the thermal pad 100-H. A divider 1910 directs the fluid flow 1920 in the pad 100-H such that the fluid flows 1920 from the inlet tube 106g into the back portion 1902, along one side of the shoulder portion 1904, down one side and up the other side of one-half of the front portion 1906, around the neck opening 1908, down one side and up the other side of the other half of the front portion 1906, along the other side of the shoulder portion 1904, and into the back portion 1902 where the fluid exits through the outlet tube 108g. The divider 1920 is configured to direct the fluid flow 1920 such that there is a relatively even distribution of fluid flow throughout the volume of the convertible vest pad 100-H.

The shoulder portion 1904 has a width that is sized to fit on the shoulders of the patient 102. The neck opening 1908 is sized to accommodate the neck of the patient 102 with the shoulder portion 1904 adjacent the patient's shoulders. In one embodiment the neck opening 1908 is sized to allow the head of the patient 102 to pass through the opening 1908.

The front portion 1906 is split into two halves by a slit 1922 between the neck opening 1908 and the bottom part of the front portion 1906. The two halves of the front portion 1906 are held together with a front fastener 1916 shown in the fastened position. In one embodiment the front fastener 1916 is a hook-and-loop fastener that allows for ready engagement and disengagement, along with the capability of adjusting the width of the split 1922 to accommodate varying torso sizes of patients 102. In other embodiments, the front fastener 1916 is a strip of flexible material with at least one button-hole or snap that engages a button or snap to secure the two halves of the front portion 1906 together. In the illustrated embodiment a single front fastener 1916 is shown adjacent the lower part of the front portion 1906. In other embodiments, one or more front fasteners 1916 are employed and positioned to secure the two halves of the front portion 1906 together.

The back portion 1902 includes one half of a pair of side fasteners 1912-A that mates with the other half of the pair of side fasteners 1912-B positioned in a corresponding location on the front portion 1906. The side fasteners 1912 join the back and front portions 1902, 1906 together such that the thermal pad 100-H is held proximate the sides of the patient 102.

The front portion 1906 includes a pair of arm fasteners 1914 that are used to secure each half of the front portion 1906 around an arm of the patient 102. One half of the front portion 1906 has one half of a arm fastener 1914-A on one side and the other half of the arm fastener 1914-B on the other side. The half of the front portion 1906 is wrapped around the arm of the patient 102 to form a cylindrical tube and the two halves of the arm fastener 1914 are joined to hold the half of the front portion 1906 together.

In another embodiment of the convertible vest pad 100-H, the fasteners 1912-A, 1914-A, 1916 are the hook portion of a hook-and-loop fastening system. The fasteners 1912-A, 1914-A, 1916 engage the non-woven material of the surfaces to secure the pad 100-H as desired.

The thermal pads 100 include various functions. The function of fastening or securing the pad 100 to itself is implemented, in one embodiment, by a hook-and-loop fastening system. In one such embodiment the fastener is the hook portion of the hook-and-loop fastening system. The hook portion adheres to the non-woven material of the surface of the pad 100. In other such embodiments, the function of fastening is implemented by a flap or strap with button holes or snaps that engage corresponding buttons or snaps.

From the foregoing description, it will be recognized by those skilled in the art that thermal pads 100 for applying temperature controlled therapy to parts of a person's body have been provided. The thermal pads 100 are configurable for specific uses with particular body parts.

In one embodiment, a head pad 100-A for providing a controlled rate of cooling to a patient 102 is disclosed, said system comprising a first surface and a second surface defining a tortuous conduit from a fluid inlet to a fluid outlet; a primary section bounded by said first surface and said second surface, said primary section including a proximal end and a distal end, and including a first edge and a second edge each between said proximal end and said distal end, said second edge opposite said first edge, said primary section dimensioned and configured to enclose a posterior of a human cranium; a first flap and a second flap each bounded by said first surface and said second surface, said first flap extending laterally from said first edge near said distal end of said primary section, said second flap extending laterally from said second edge near said distal end of said primary section, a distal portion of said first flap releasably fastenable to a distal portion of said second flap; a third flap and a fourth flap each bounded by said first surface and said second surface, said third flap extending laterally from said first edge near said proximal end of said primary section, said fourth flap extending laterally from said second edge near said proximal end of said primary section, a distal portion of said third flap releasably fastenable to a distal portion of said fourth flap; a fifth flap and a sixth flap each bounded by said first surface and said second surface, said fifth flap adjacent to said sixth flap, said fifth flap extending from said distal end of said primary section, such that a distal portion of said fifth flap is releasably fastenable to said first flap or said second flap, said sixth flap extending from said distal end of said primary section, such that a distal portion of said sixth flap is releasably fastenable to said first flap or said second flap; whereby said pad encloses said cranium when said first and second flaps are fastened to each other, and when said third and fourth flaps are fastened to each other, and when said fifth and sixth flaps are fastened to at least one of said first and second flaps.

In one such embodiment, said first flap and said second flap are dimensioned and configured to extend around a human skull and enclose at least a portion of a human forehead. In another such embodiment, said third flap and said fourth flap are dimensioned and configured to extend around a human neck. In another such embodiment, said fifth flap and said sixth flap are dimensioned and configured to extend from said distal end of said primary section and across a human cranium. In another such embodiment, further comprising a first opening and a second opening, said first opening defined by a first area between said first flap and said third flap, said second opening defined by a second area between said second flap and said fourth flap, each of said first opening and said second opening dimensioned and configured to be proximate an ear of a human head when said pad is being worn. In another such embodiment, said pad includes an outer layer including a layer of foam, an inner layer, and a pair of waterproof sheets therebetween, said outer layer, said inner layer, and said pair of waterproof sheets joined together at selective locations to define said tortuous conduit between said pair of waterproof sheets. In another such embodiment, further comprising a cooling device, said cooling device having a pump in a fluid reservoir, said pump having an outlet in fluid communication with said fluid inlet of said pad, said fluid outlet of said pad in fluid communication with said fluid reservoir, and said fluid inlet and said fluid outlet releasably connected to said cooling device. In another such embodiment, further including a second pad, said second pad including an inner surface and an outer surface defining a second tortuous conduit from a second fluid inlet to a second fluid outlet; a first section bounded by said inner surface and said outer surface, said first section having substantially a first one-fourth prolate spheroid shape, and having a first pair of edges that connect at both ends of said first section; and a second section bounded by said inner surface and said outer surface, said second section having substantially a second one-fourth prolate spheroid shape, and having a second pair of edges that connect at both ends of said second section, said second section joined to said first section along at least a portion of one of said first pair of edges and at least a portion of one of said second pair of edges, said second section in fluid communication with said first section, wherein said joined edges provide for positioning the second pad to enclose a selectable portion of a human head.

In one embodiment, a head pad 100-A for providing a controlled rate of cooling to a patient, said pad comprising a first surface and a second surface defining a tortuous conduit from a fluid inlet to a fluid outlet; a primary section bounded by said first surface and said second surface, said primary section including a proximal end, a distal end, a pair of edges between said proximal end and said distal end, said pair of edges opposite each other, said primary section dimensioned and configured to enclose a posterior of a human cranium; a first pair of flaps bounded by said first surface and said second surface, each of said first pair of flaps extending from one of said pair of edges near said distal end of said primary section, a distal portion of said first pair of flaps releasably fastenable to each other; a second pair of flaps bounded by said first surface and said second surface, each of said second pair of flaps extending from one of said pair of edges near said proximal end of said primary section, a distal portion of said second pair of flaps releasably fastenable to each other; a third pair of flaps bounded by said first surface and said second surface, each of said third pair of flaps extending from said distal end of said primary section, a distal portion of each of said third pair of flaps releasably fastenable to at least one of said first pair of flaps; whereby said pad encloses said cranium when said first pair of flaps are fastened to each other, and when said second pair of flaps are fastened to each other, and when said third pair of flaps are fastened to at least one of said first pair of flaps.

In one such embodiment, said first pair of flaps are dimensioned and configured to extend around a human skull and enclose at least a portion of a human forehead. In another such embodiment, said third pair of flaps are dimensioned and configured to extend from said distal end of said primary section and across a human cranium. In another such embodiment, further comprising a pair of openings, each defined by a respective area between a corresponding pair of flaps, one each from said first pair of flaps and from said second pair of flaps, each opening dimensioned and configured to be proximate an ear of a human head when said pad is being worn. In another such embodiment, said pad includes an outer layer including a layer of foam, an inner layer, and a pair of waterproof sheets therebetween, said outer layer, said inner layer, and said pair of waterproof sheets joined together at selective locations to define said tortuous conduit between said pair of waterproof sheets.

In one embodiment, a cap pad 100-C for providing a controlled rate of cooling to a patient, said pad comprising a first surface and a second surface, said first surface and said second surface defining a tortuous conduit from a fluid inlet to a fluid outlet; a first section bounded by said first surface and said second surface, said first section having substantially a first one-fourth prolate spheroid shape, and having a first edge and a second edge that connect at both ends of said first section; and a second section bounded by said first surface and said second surface, said second section having substantially a second one-fourth prolate spheroid shape, and having a first edge and a second edge that connect at both ends of said second section, said second section joined to said first section along at least a portion of said first edge of said first section and at least a portion of said first edge of said second section, said second section in fluid communication with said first section, wherein said joined edges provide for positioning the pad to enclose a selectable portion of a human head.

In one such embodiment, each section further including an opening defining a location for an eye of the patient. One such embodiment further including a crease line extending through said openings between said second edge of said first section and said second edge of said second section, wherein said crease line defines separate portions of the pad, and wherein each portion is foldable away from the patient. In another such embodiment, further including a central opening defining a location for a nose of the patient. In another such embodiment, further including a base opening proximate a base of said section and defining a location for a mouth of the patient. One such embodiment further including a bifurcated opening, said bifurcated opening defining said sections, said bifurcated opening extending from proximate said base opening to a distal end of the pad. In another such embodiment, a cooling device, said cooling device having a pump in a fluid reservoir, said pump having an outlet in fluid communication with said fluid inlet of said pad, said fluid outlet of said pad in fluid communication with said fluid reservoir, and said fluid inlet and said fluid outlet releasably connected to said cooling device.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for providing temperature controlled therapy to an upper body of a patient, said apparatus comprising:
    a back portion dimensioned and configured to cover a substantial portion of a back of the patient;
    a front portion dimensioned and configured to cover a substantial portion of a front of the patient, said front portion divided into two sections;

a shoulder portion connecting said back portion and said front portion, said shoulder portion having an opening dimensioned and configured to fit around a neck of the patient;

a pair of side fasteners positioned to join each side of said back portion to a corresponding side of said front portion;

each section of said front portion including an arm fastener positioned to join opposing sides of said each section of said front portion to form a tube sized and configured to wrap around an arm of the patient;

wherein said apparatus includes an inner surface and an outer surface defining a pad with a tortuous conduit from a fluid inlet to a fluid outlet, said pad including said back, front, and shoulder portions.

2. The apparatus of claim 1 wherein said apparatus has a vest-type configuration when said pair of side fasteners join each side of said back portion to a corresponding side of said front portion.

3. The apparatus of claim 2 further including a front fastener positioned to join said two sections to each other when said apparatus is in said vest-type configuration.

4. The apparatus of claim 1 wherein said fluid inlet and said fluid outlet are connected to said back portion.

5. The apparatus of claim 1 further including an innermost layer, a pair of middle layers, and an outermost layer joined together, said innermost layer including a first non-woven material and having said inner surface, said pair of middle layers being water proof, said pair of middle layers defining said tortuous conduit, and said outermost layer including a second non-woven material and having said outer surface.

6. The apparatus of claim 1 wherein said pad includes a divider configured to direct a flow of fluid from said fluid inlet to said fluid outlet such that said flow of fluid is distributed throughout said pad.

7. The apparatus of claim 1 wherein said pad includes a divider defining a channel between said divider and an edge of said pad, and said channel directing a flow of fluid from said fluid inlet to said fluid outlet such that said flow of fluid is distributed throughout said pad.

8. An apparatus that is a garment for providing temperature controlled therapy to an upper body of a patient, said apparatus comprising:

a pad defined by an inner surface and an outer surface, said inner surface and said outer surface defining a tortuous conduit from a fluid inlet to a fluid outlet, said pad including a back portion dimensioned and configured to cover a substantial portion of a back of the patient, said pad including a front portion dimensioned and configured to cover a substantial portion of a front of the patient, said front portion divided into two sections, said pad including a shoulder portion connecting said back portion and said front portion, said shoulder portion having an opening dimensioned and configured to fit around a neck of the patient, said pad having a first configuration wherein said front portion has a vest-type configuration that is configured to be positioned proximate a chest of the patient, and said pad having a second configuration wherein each one of said sections of said front portion is configured to cover an arm of the patient.

9. The apparatus of claim 8 further including a pair of side fasteners positioned to join each side of said back portion to a corresponding side of said front portion.

10. The apparatus of claim 8 further including a pair of arm fasteners each positioned to join opposing sides of said each section of said front portion to form a tube sized and configured to cover a corresponding arm of the patient.

11. The apparatus of claim 8 wherein said pad includes a divider configured to direct a flow of fluid from said fluid inlet to said fluid outlet such that said flow of fluid is distributed throughout said pad.

12. The apparatus of claim 8 further including an innermost layer, a pair of middle layers, and an outermost layer joined together, said innermost layer including a first non-woven material and having said inner surface, said pair of middle layers being water proof, said pair of middle layers defining said tortuous conduit, and said outermost layer including a second non-woven material and having said outer surface.

13. The apparatus of claim 8 wherein said pad includes a divider defining a channel between said divider and an edge of said pad, and said channel configured to direct a flow of fluid from said fluid inlet to said fluid outlet such that said flow of fluid is distributed throughout said pad.

* * * * *